US012740726B2

(12) United States Patent
Kim et al.

(10) Patent No.: US 12,740,726 B2
(45) Date of Patent: Sep. 22, 2026

(54) METHOD AND APPARATUS FOR NON-INVASIVE ESTIMATION OF GLYCATED HEMOGLOBIN OR BLOOD GLUCOSE BY USING MACHINE LEARNING

(71) Applicant: KOREA I.T.S. CO., LTD., Seoul (KR)

(72) Inventors: Ki Doo Kim, Seoul (KR); Tae Ho Kwon, Goyang-si (KR)

(73) Assignee: KOREA I.T.S. CO., LTD., Seoul (KR)

( * ) Notice: Subject to any disclaimer, the term of this patent is extended or adjusted under 35 U.S.C. 154(b) by 323 days.

(21) Appl. No.: 18/405,491

(22) Filed: Jan. 5, 2024

(65) Prior Publication Data

US 2024/0148282 A1 May 9, 2024

Related U.S. Application Data

(63) Continuation of application No. PCT/KR2022/009639, filed on Jul. 5, 2022.

(30) Foreign Application Priority Data

Sep. 8, 2021 (KR) ........................ 10-2021-0119524

(51) Int. Cl.
*A61B 5/145* (2006.01)
*A61B 5/00* (2006.01)
(Continued)

(52) U.S. Cl.
CPC ...... *A61B 5/14532* (2013.01); *A61B 5/02416* (2013.01); *A61B 5/1455* (2013.01); *A61B 5/7267* (2013.01); *A61B 5/7278* (2013.01)

(58) Field of Classification Search
CPC . A61B 5/14532; A61B 5/1455; A61B 5/1477; A61B 5/02416; A61B 5/7267; A61B 5/7278; A61B 5/7264
See application file for complete search history.

(56) References Cited

U.S. PATENT DOCUMENTS

2009/0326342 A1* 12/2009 Huiku ................ A61B 5/14551 600/322
2016/0324477 A1* 11/2016 Gunturi .................. A61B 5/721
(Continued)

FOREIGN PATENT DOCUMENTS

EP 2544124 A1 * 1/2013 ........... A61B 5/1455
KR 10-0871074 B1 11/2008
(Continued)

OTHER PUBLICATIONS

Haque et al.; "Noninvasive In Vivo Estimation of Blood-Glucose Concentration by Monte Carlo Simulation"; Sensors; vol. 21; article No. 4918; Jul. 19, 2021; pp. 1-18.
(Continued)

*Primary Examiner* — Devin B Henson
(74) *Attorney, Agent, or Firm* — Studebaker Brackett PLLC

(57) ABSTRACT

The present disclosure relates to a method and apparatus for non-invasive estimation of glycated hemoglobin (HbA1c) or blood glucose by using machine learning, the method comprising: a signal collection stage of collecting a bio-signal of a measurement subject to be measured; a feature extraction stage of extracting a plurality of features from the bio-signal; a machine learning model construction stage of constructing a machine learning model for estimating glycated hemoglobin or blood glucose by learning training data including the plurality of features; and a glycated hemoglobin/blood glucose estimation stage of generating input data on the basis of the bio-signal extracted from the measurement subject being measured and inputting the input data to the machine learning model, so as to estimate glycated hemoglobin or blood glucose of the measurement subject being measured.

8 Claims, 12 Drawing Sheets

(51) Int. Cl.
*A61B 5/024* (2006.01)
*A61B 5/1455* (2006.01)

(56) References Cited

U.S. PATENT DOCUMENTS

2021/0401330 A1* 12/2021 Frank .................... A61B 5/746
2023/0355143 A1* 11/2023 Tang .................... A61B 5/7203

FOREIGN PATENT DOCUMENTS

KR 10-2021-0078662 A 6/2021
KR 10-2021-0091559 A 7/2021
KR 10-2021-0101895 A 8/2021
KR 10-2021-0101898 A 8/2021

OTHER PUBLICATIONS

International Search Report issued in PCT/KR2022/009639; mailed Oct. 21, 2022.
Written Opinion of the International Searching Authority issued in PCT/KR2022/009639; mailed Oct. 21, 2022.

* cited by examiner

FIG. 8A

| | 18 features | | | | 7 features | | | |
|---|---|---|---|---|---|---|---|---|
| | Random Forest | | XGBoost | | Random Forest | | XGBoost | |
| | R | T | R | T | R | T | R | T |
| Diff STD | 0.523 | 0.675 | 0.321 | 0.439 | 0.481 | 0.576 | **0.278** | 0.368 |
| MSE | 0.279 | 0.467 | 0.105 | 0.195 | 0.239 | 0.341 | **0.089** | 0.139 |
| ME | -0.075 | -0.106 | 0.039 | 0.051 | -0.088 | -0.096 | **0.108** | 0.058 |
| MAD | 0.404 | 0.483 | 0.220 | 0.276 | 0.380 | 0.440 | **0.201** | 0.260 |
| RMSE | 0.529 | 0.683 | 0.324 | 0.442 | 0.489 | 0.584 | **0.298** | 0.373 |
| $R^2$ score | 0.685 | 0.473 | 0.881 | 0.780 | 0.730 | 0.615 | **0.900** | 0.843 |
| Pearson's r | 0.831 | 0.709 | 0.942 | 0.884 | 0.862 | 0.791 | **0.957** | 0.921 |

| | 18 features | | | | 7 features | | | |
|---|---|---|---|---|---|---|---|---|
| | Random Forest | | XGBoost | | Random Forest | | XGBoost | |
| | R | T | R | T | R | T | R | T |
| Diagnostic performance | 77.5 | 70 | 90 | 87.5 | 80 | 80 | **92.5** | 85 |

FIG. 8B

| | 17 features | | | | 6 features | | | |
|---|---|---|---|---|---|---|---|---|
| | Random Forest | | XGBoost | | Random Forest | | XGBoost | |
| | R | T | R | T | R | T | R | T |
| Diff STD | 0.72 | 0.61 | 0.6 | 0.63 | 0.66 | 0.583 | **0.57** | 0.56 |
| MSE | 0.51 | 0.37 | 0.36 | 0.39 | 0.44 | 0.29 | **0.33** | 0.31 |
| ME | -0.04 | 0.04 | -0.2 | -0.01 | 0.0004 | -0.05 | **0.09** | -0.001 |
| MAD | 0.53 | 0.49 | 0.44 | 0.47 | 0.52 | 0.42 | **0.41** | 0.39 |
| RMSE | 0.72 | 0.61 | 0.60 | 0.63 | 0.66 | 0.53 | **0.57** | 0.56 |
| $R^2$ score | 0.42 | 0.58 | 0.6 | 0.56 | 0.50 | 0.68 | **0.63** | 0.65 |
| Pearson's r | 0.65 | 0.76 | 0.77 | 0.75 | 0.71 | 0.83 | **0.80** | 0.81 |

| | 17 features | | | | 6 features | | | |
|---|---|---|---|---|---|---|---|---|
| | Random Forest | | XGBoost | | Random Forest | | XGBoost | |
| | R | T | R | T | R | T | R | T |
| Diff STD | 25.5 | 28.05 | 17.21 | 18.94 | 21.68 | 26.59 | **10.08** | 18.35 |
| MSE | 650.01 | 786.71 | 296.03 | 358.9 | 472.29 | 736.94 | **106.81** | 348.82 |
| ME | 2.47 | 4.06 | 3.79 | 4.32 | 1.52 | 5.46 | **2.3** | 3.5 |
| MAD | 19.61 | 20.62 | 13.09 | 13.39 | 16.83 | 20.87 | **7.58** | 14.12 |
| RMSE | 25.5 | 28.05 | 17.21 | 18.94 | 21.73 | 27.15 | **10.33** | 18.68 |
| $R^2$ score | 0.25 | 0.09 | 0.66 | 0.58 | 0.45 | 0.14 | **0.88** | 0.6 |
| Pearson's r | 0.51 | 0.37 | 0.85 | 0.8 | 0.67 | 0.43 | **0.94** | 0.81 |

| | 17 features | | | | 6 features | | | |
|---|---|---|---|---|---|---|---|---|
| | Random Forest | | XGBoost | | Random Forest | | XGBoost | |
| | R | T | R | T | R | T | R | T |
| Diagnostic performance | 0.73 | 65.4 | 84.6 | 80.8 | 80.8 | 69.2 | **92.3** | 80.8 |

FIG. 11
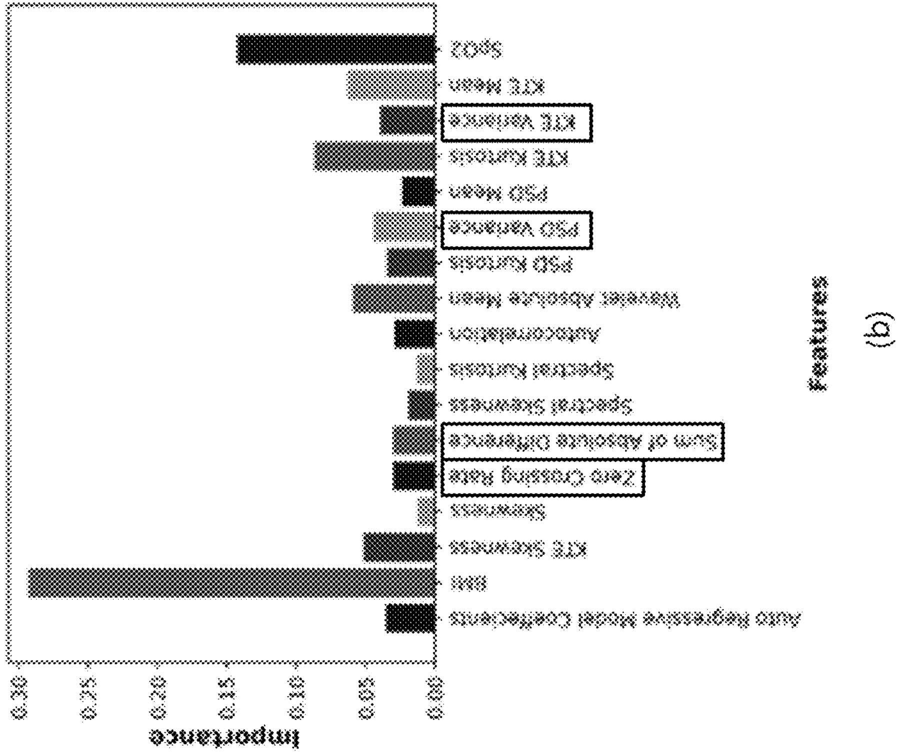
(b)
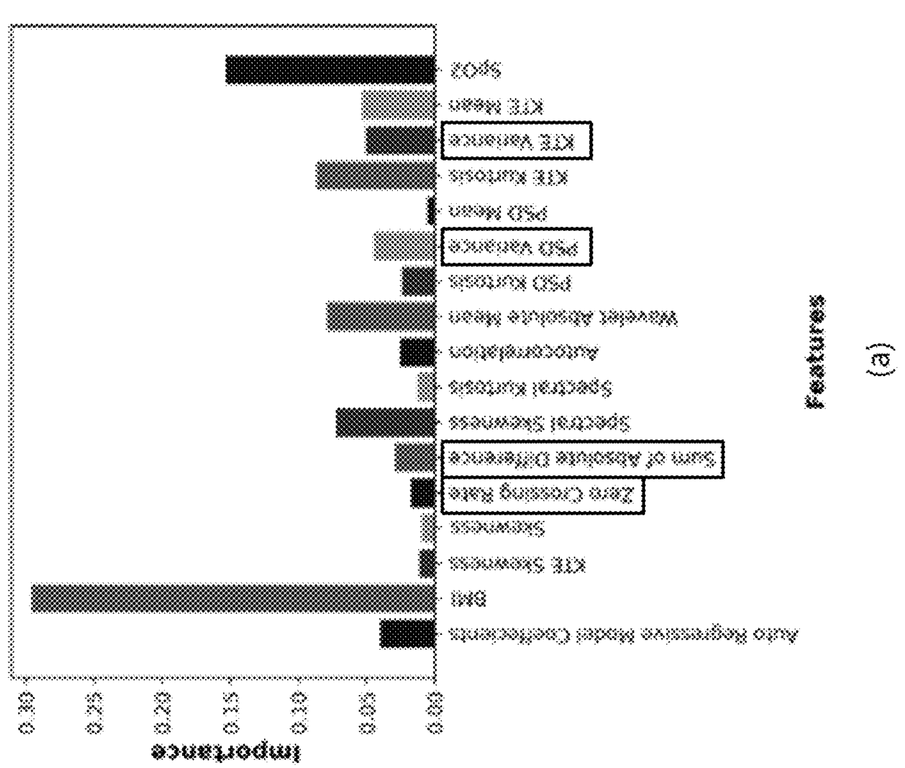
(a)

METHOD AND APPARATUS FOR NON-INVASIVE ESTIMATION OF GLYCATED HEMOGLOBIN OR BLOOD GLUCOSE BY USING MACHINE LEARNING

CROSS-REFERENCE TO RELATED APPLICATIONS

The present application is a continuation of International Patent Application No. PCT/KR2022/009639, filed on Jul. 5, 2022, which is based upon and claims the benefit of priority to Korean Patent Application No. 10-2021-0119524 filed on Sep. 8, 2021. The disclosures of the above-listed applications are hereby incorporated by reference herein in their entirety.

TECHNICAL FIELD

The present disclosure relates to a non-invasive glycated hemoglobin or blood glucose estimation technology, and more specifically, to a method and apparatus for non-invasive estimation of glycated hemoglobin or blood glucose by using machine learning capable of more accurately estimating glycated hemoglobin or blood glucose non-invasively by learning various pieces of feature information extracted from a bio-signal of a measurement subject being measured.

BACKGROUND ART

Diabetes is a metabolic disease characterized by hyperglycemia caused by dysfunction or secretion of insulin, which is necessary for controlling blood glucose levels in the body. Chronic hyperglycemia due to diabetes causes damage and functional insufficiency in each organ of the body. In particular, the chronic hyperglycemia causes microvascular complications of the retina, kidneys, and nerves, and macrovascular complications such as arteriosclerosis, cardiovascular, and cerebrovascular diseases, resulting in an increase in mortality.

However, diabetes may reduce the worsening or complication rate of diabetes due to blood glucose control, weight loss, and medication. Accordingly, diabetic patients need to frequently measure their own blood glucose levels to manage their blood glucose levels and undergo regular glycated hemoglobin (HbA1C) tests, which are as important a treatment indicator as the blood glucose levels of the diabetic patients.

The glycated hemoglobin (HbA1c) test is a test that determines the extent to which the hemoglobin in red blood cells, which plays a role in transporting oxygen in the blood, has been glycated. Depending on the average lifespan of red blood cells, the test reflects changes in blood glucose over the past 2 to 3 months. Since glucose always exists in normal people, hemoglobin is glycated to some extent in the blood. The normal value varies depending on a test method, but usually up to 5.6% is normal.

In diabetic patients, as the concentration of glucose in the blood increases, glycated hemoglobin, in other words, the level of glycated hemoglobin, also increases. Accordingly, the direction of future treatment is decided by reviewing these results, which clearly reveal the extent of blood glucose control so far.

The conventional method of measuring glycated hemoglobin (HbA1c) is to acquire a capillary blood sample by collecting blood from a vein in the arm of a measurement subject being measured measurement subject or pricking the tip of the finger with a small and pointed needle, and use the acquired blood to measure the concentration of glycated hemoglobin (HbA1c). The invasive method of measuring glycated hemoglobin has an issue of increasing the burden of blood collection on measurement subjects to be measured and providing inaccurate levels in cases of short red blood cell lifespan, pregnancy, or kidney disease.

RELATED ART DOCUMENT

Patent Document

Korean Patent No. 10-0871074 (Nov. 24, 2008)

DETAILED DESCRIPTION OF INVENTION

Technical Problem

An embodiment of the present disclosure is directed to providing a method and apparatus for non-invasive estimation of glycated hemoglobin or blood glucose by using machine learning capable of more accurately estimating glycated hemoglobin or blood glucose non-invasively by learning various pieces of feature information extracted from a bio-signal of a measurement subject being measured.

An embodiment of the present disclosure is directed to providing a method and apparatus for non-invasive estimation of glycated hemoglobin or blood glucose by using machine learning capable of constructing a learning model for non-invasive estimation of glycated hemoglobin or blood glucose by collecting enough data for learning from machine learning, such as various age groups, patients, and genders, and combining the unique advantages of individual feature vectors.

Technical Solution

In an embodiment, a method for non-invasive estimation of glycated hemoglobin (HbA1c) or blood glucose by using machine learning includes: a signal collection stage of collecting a bio-signal of a measurement subject being measured; a feature extraction stage of extracting a plurality of features from the bio-signal; a machine learning model construction stage of constructing a machine learning model for estimating glycated hemoglobin or blood glucose by learning training data including the plurality of features; and a glycated hemoglobin/blood glucose estimation stage of generating input data on the basis of the bio-signal extracted from the measurement subject being measured and inputting the input data to the machine learning model, so as to estimate glycated hemoglobin or blood glucose of the measurement subject being measured.

The signal collection stage may include measuring PPG signals of the measurement subject being measured and collecting the same as the bio-signal.

The signal collection stage may include: irradiating a body part of the measurement subject being measured with light through an LED module positioned on one side of the body part; detecting transmitted light transmitting the body part or reflected light reflected from the body part through a photo detector positioned corresponding to the LED module; and measuring the PPG signals based on a change in intensity of the transmitted light or the reflected light.

The feature extraction stage may include collecting external features directly measured from the measurement subject being measured along with internal features extracted directly from the PPG signals and determining the same as the plurality of features.

The feature extraction stage may include: extracting, based on the PPG signals, Zero-Crossing Rate (ZCR), Auto Correlation, Power Spectral Density (PSD), Kaiser-Teager energy (KTE), Spectral Analysis (SA), Wavelet Analysis (WA), Autoregressive Coefficients (ARC), Heart Rate (HR), and Breathing Rate (BR) as the internal features; and collecting Body Mass Index (BMI), Finger Width (FW), and Saturation Pulse Oxygen (SpO2) as the external features.

The feature extraction stage may include: determining at least one representative feature among the internal features according to importance; and determining the plurality of features by adding at least one of the external features to the representative features.

The machine learning model may include a machine learning model trained using Random Forest or XGBoost algorithm.

The glycated hemoglobin/blood glucose estimation stage may include analyzing the glycated hemoglobin or blood glucose to determine a diabetes grade of the measurement subject being measured.

In an embodiment, an apparatus for non-invasive estimation of glycated hemoglobin (HbA1c) or blood glucose by using machine learning includes: a signal collection unit of collecting a bio-signal of a measurement subject being measured; a feature extraction unit of extracting a plurality of features from the bio-signal; a model construction unit of constructing a machine learning model for estimating glycated hemoglobin or blood glucose by learning training data including the plurality of features; and a glycated hemoglobin/blood glucose estimation unit of generating input data on the basis of the bio-signal extracted from the measurement subject being measured and inputting the input data to the machine learning model, so as to estimate glycated hemoglobin or blood glucose of the measurement subject being measured.

The feature extraction unit may collect external features directly measured from the measurement subject being measured along with internal features extracted directly from the PPG signals and determine the same as the plurality of features.

The feature extraction unit may: extract, based on the PPG signals, Zero-Crossing Rate (ZCR), Auto Correlation, Power Spectral Density (PSD), Kaiser-Teager energy (KTE), Spectral Analysis (SA), Wavelet Analysis (WA), Autoregressive Coefficients (ARC), Heart Rate (HR), and Breathing Rate (BR) as the internal features; and collect Body Mass Index (BMI), Finger Width (FW), and Saturation Pulse Oxygen (SpO2) as the external features.

The feature extraction unit may: determine at least one representative feature among the internal features according to importance; and determine the plurality of features by adding at least one of the external features to the representative features.

Advantageous Effects

The disclosed technology may have the following effects. However, it does not mean that a specific exemplary embodiment should include the entire following effects or should include only the following effects, and it should not be understood that the scope of right of disclosed technology is limited thereto.

A method and apparatus for non-invasive estimation of glycated hemoglobin by using machine learning according to an embodiment of the present disclosure can non-invasively estimate glycated hemoglobin or blood glucose more accurately by learning various pieces of feature information extracted from a bio-signal of a measurement subject being measured.

A method and apparatus for non-invasive estimation of glycated hemoglobin or blood glucose by using machine learning according to an embodiment of the present disclosure can construct a learning model for non-invasive estimation of glycated hemoglobin or blood glucose by collecting enough data for learning from machine learning, such as various age groups, patients, and genders, and combining the unique advantages of individual feature vectors.

BRIEF DESCRIPTION OF THE DRAWINGS

FIGS. 8A and 8B are diagrams illustrating performance comparison regarding glycated hemoglobin estimation according to an embodiment of the present disclosure.

FIG. 10 is a diagram explaining performance comparison regarding blood glucose estimation according to an embodiment of the present disclosure.

FIG. 11 is a diagram illustrating a feature importance graph related to blood glucose estimation according to an embodiment of the present disclosure.

DESCRIPTION OF EXEMPLARY EMBODIMENTS

Figure 1:
FIG. 1 is a diagram illustrating a system for estimation of glycated hemoglobin or blood glucose according to an embodiment of the present disclosure.
Figure 1:
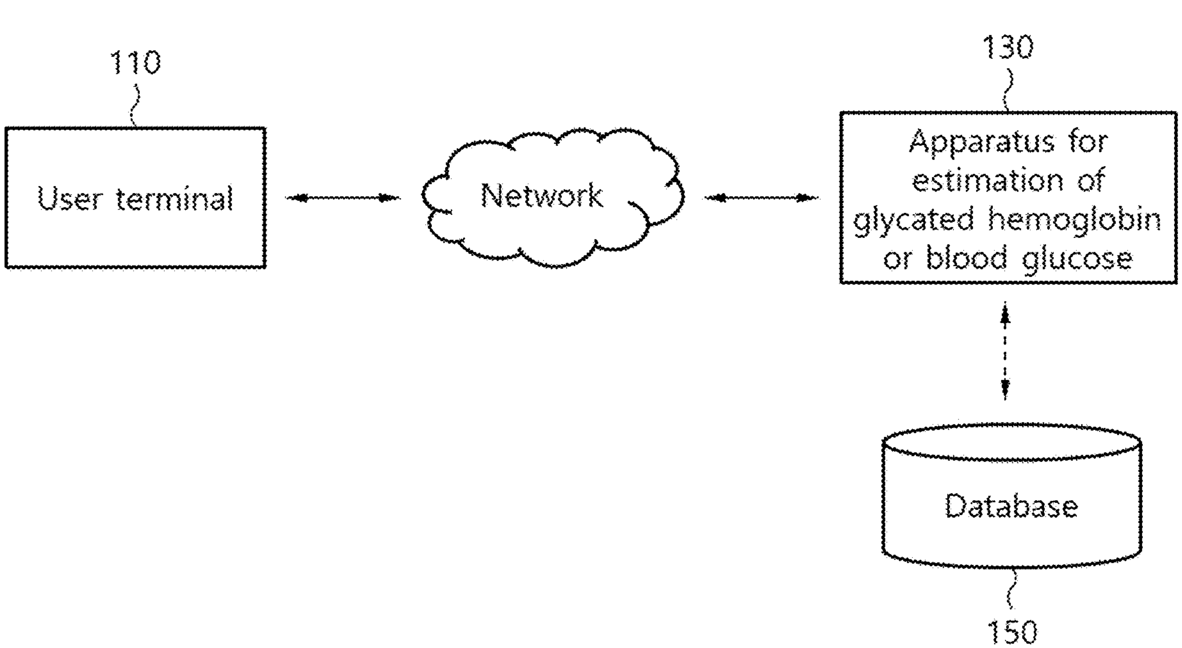

The explanation of the present disclosure is merely an embodiment for structural or functional explanation, so the scope of the present disclosure should not be construed to be limited to the embodiments explained in the embodiment. That is, since the embodiments may be implemented in several forms without departing from the characteristics thereof, it should also be understood that the described embodiments are not limited by any of the details of the foregoing description, unless otherwise specified, but rather should be construed broadly within its scope as defined in the appended claims. Therefore, various changes and modifications that fall within the scope of the claims, or equivalents of such scope are therefore intended to be embraced by the appended claims.

Terms described in the present disclosure may be understood as follows.

While terms such as “first”, “second”, etc., may be used to describe various components, such components must not be understood as being limited to the above terms. The above terms are used to distinguish one component from another. For example, a first component may be referred to as a second component without departing from the scope of rights of the present disclosure, and likewise a second component may be referred to as a first component.

It will be understood that when an element is referred to as being "connected to" another element, it may be directly connected to the other element or intervening elements may also be present. In contrast, when an element is referred to as being "directly connected to" another element, no intervening elements are present. In addition, unless explicitly described to the contrary, the word "comprise" and variations such as "comprises" or "comprising" will be understood to imply the inclusion of stated elements but not the exclusion of any other elements. Meanwhile, other expressions describing relationships between components such as "between", "immediately between" or "adjacent to" and "directly adjacent to" may be construed similarly.

Singular forms "a", "an" and "the" in the present disclosure are intended to include the plural forms as well, unless the context clearly indicates otherwise. It will be further understood that terms such as "including" or "having", etc., are intended to indicate the existence of the features, numbers, operations, actions, components, parts, or combinations thereof disclosed in the specification, and are not intended to preclude the possibility that one or more other features, numbers, operations, actions, components, parts, or combinations thereof may exist or may be added.

In each phase, reference numerals (for example, a, b, c, etc.) are used for the sake of convenience in description, and such reference numerals do not describe the order of each phase. The order of each phase may vary from the specified order, unless the context clearly indicates a specific order. In other words, each phase may take place in the same order as the specified order, may be performed substantially simultaneously, or may be performed in a reverse order.

The present disclosure may be implemented as machine-readable codes on a machine-readable medium. The machine-readable medium may include any type of recording device for storing machine-readable data. Examples of the machine-readable recording medium may include a read-only memory (ROM), a random access memory (RAM), a compact disk-read only memory (CD-ROM), a magnetic tape, a floppy disk, optical data storage, or any other appropriate type of machine-readable recording medium. The medium may also be carrier waves (for example, Internet transmission). The computer-readable recording medium may be distributed among networked machine systems which store and execute machine-readable codes in a de-centralized manner.

The terms used in the present application are merely used to describe particular embodiments, and are not intended to limit the present disclosure. Unless otherwise defined, all terms used herein, including technical or scientific terms, have the same meanings as those generally understood by those with ordinary knowledge in the field of art to which the present disclosure belongs. Such terms as those defined in a generally used dictionary are to be interpreted to have the meanings equal to the contextual meanings in the relevant field of art, and are not to be interpreted to have ideal or excessively formal meanings unless clearly defined in the present application.

FIG. 1 is a diagram illustrating a system for estimation of glycated hemoglobin or blood glucose according to an embodiment of the present disclosure.

Referring to FIG. 1, a system 100 for estimation of glycated hemoglobin or blood glucose may include a user terminal 110, an apparatus 130 for estimation of glycated hemoglobin or blood glucose, and a database 150.

The user terminal 110 may correspond to a computing device that may provide data for machine learning and check the results of non-invasive estimation of glycated hemoglobin. For example, a user may input information about his/her bio-signal through the user terminal 110 and check the glycated hemoglobin or blood glucose information estimated by a machine learning model. In an embodiment, the user terminal 110 may directly measure bio-signals from the user. For example, the user terminal 110 may install and execute a dedicated application for measuring bio-signals, and through this, PPG signals related to the bio-signals of the use may be collected.

In addition, the user terminal 110 may be implemented as a smartphone, laptop, or computer that may be operated by being connected to the apparatus 130 for estimation of glycated hemoglobin or blood glucose, but is not necessarily limited thereto, and may also be implemented as a variety of devices such as a tablet PC. The user terminal 110 may be connected to the apparatus 130 for estimation of glycated hemoglobin or blood glucose through a wired or wireless network, and a plurality of user terminals 110 may be simultaneously connected to the apparatus 130 for estimation of glycated hemoglobin or blood glucose.

The apparatus 130 for estimation of glycated hemoglobin or blood glucose may be implemented as a server corresponding to a computer or program that may construct a machine learning model for estimation of glycated hemoglobin or blood glucose and perform operations related to non-invasive estimation of glycated hemoglobin or glucose based thereon. The apparatus 130 for estimation of glycated hemoglobin or blood glucose may be connected to the user terminal 110 through a wireless network such as Bluetooth or Wi-Fi, and may transmit and receive data with the user terminal 110 through the network. In addition, the apparatus 130 for estimation of glycated hemoglobin or blood glucose may also be implemented to operate in conjunction with a separate external system (not shown in FIG. 1) to collect data or provide additional functions.

The database 150 may correspond to a storage device that stores various pieces of information required during the operation of the apparatus 130 for estimation of glycated hemoglobin or blood glucose. For example, the database 150 may store information about bio-signals collected from a user, and may store information about machine learning models constructed through learning, but is not necessarily limited thereto, and may store information collected or processed in various forms during the process of the apparatus 130 for estimation of glycated hemoglobin or blood glucose non-invasively performing a method for estimation of glycated hemoglobin or blood glucose using machine learning.

In FIG. 1, the database 150 is illustrated as a device independent of the apparatus 130 for estimation of glycated hemoglobin or blood glucose, but is not necessarily limited thereto, and is a logical storage device of the apparatus 130 for estimation of glycated hemoglobin or blood glucose and may be implemented by being included in the apparatus 130 for estimation of glycated hemoglobin or blood glucose.

Figure 2:
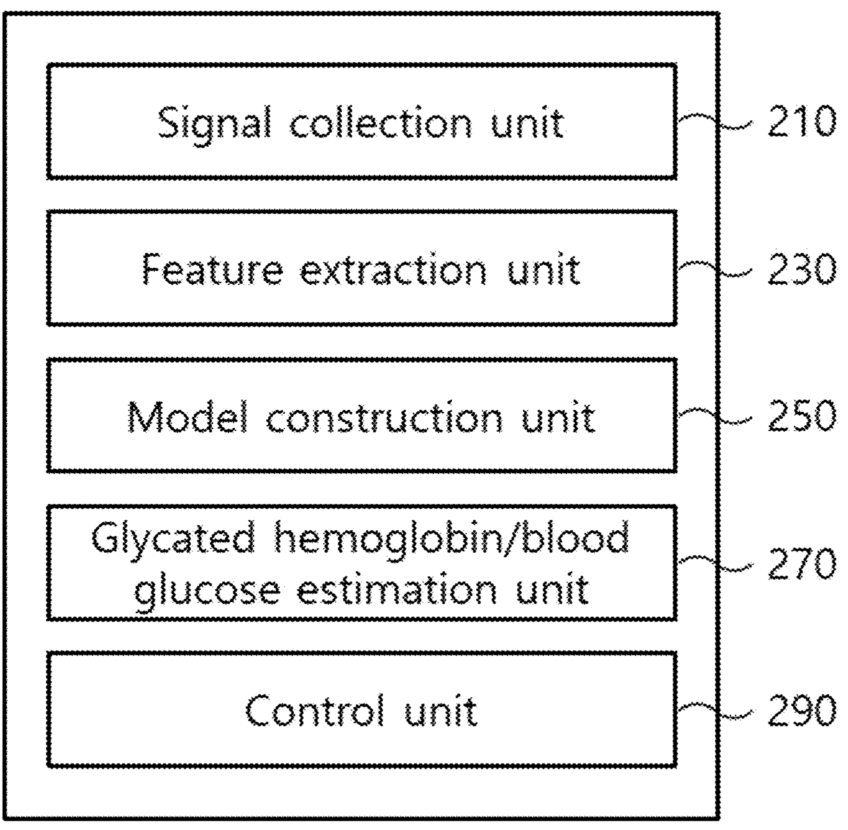
FIG. 2 is a diagram illustrating the functional configuration of an apparatus for estimation of the glycated hemoglobin or blood glucose of FIG. 1.

FIG. 2 is a diagram illustrating the functional configuration of an apparatus for estimation of the glycated hemoglobin or blood glucose of FIG. 1.

Referring to FIG. 2, the apparatus 130 for estimation of glycated hemoglobin or blood glucose may include a signal collection unit 210, a feature extraction unit 230, a model construction unit 250, a glycated hemoglobin/blood glucose estimation unit 270, and a control unit 290.

The signal collection unit 210 may collect bio-signals of a measurement subject being measured. The bio-signals are biological signals generated from the activities of living cells and may mainly correspond to electric and magnetic signals. Since the size of the signal is very small, precise measurement technology is required. For example, the bio-signals may include information that may be collected from the measurement subject being measured through various measurement devices, such as body temperature, pulse, blood pressure, respiration, blood glucose, brain waves, electrocardiogram, and oxygen saturation. The signal collection unit 210 may perform a collection operation related to bio-signals in conjunction with the user terminal 110, and, if necessary, may operate in conjunction with an independent device for measuring bio-signals. The signal collection unit 210 may measure bio-signals by directly contacting the body of the measurement subject being measured, depending on the type of measurement device.

In an embodiment, the signal collection unit 210 may measure PPG signals of the measurement subject being measured and collect the same as bio-signals. In other words, the signal collection unit 210 may collect the PPG signals in real time through a dedicated device for measuring the PPG signals of the measurement subject being measured and store the same in the database 150. Hereinafter, a specific embodiment of collecting the PPG signals will be described, without being necessarily limited thereto, and the signal collection unit 210 may measure the PPG signals in various ways.

In an embodiment, the signal collection unit 210 may perform a plurality of stages to non-invasively collect the PPG signals from the measurement subject being measured. More specifically, the signal collection unit 210 may: irradiate light toward a body part through an LED module positioned on one side of the body part of the measurement subject being measured; detect transmitted light that transmits the body part or reflected light that is reflected on the body part through a photo detector positioned corresponding to the LED module; and measure the PPG signals based on a change in intensity of the transmitted light or reflected light.

Herein, the LED module may be implemented as a light source capable of projecting light having a specific wavelength, and may be formed in a singular or plural number. When formed in a plural number, each LED module may project light having different wavelengths. The LED module may be installed on one side of the body part of the measurement subject being measured. For example, the LED module may be installed on one side of the body part of the measurement subject being measured, such as the fingers, wrist, forehead, cheek, or ear, without being necessarily limited thereto, and may include various body parts capable of sensing capillaries existing under the skin depending on installation conditions and skin thickness.

In addition, the photo detector may correspond to a device that may measure lights projected from an LED module. The photo detector may be installed in a position corresponding to the position of the LED module. For example, the photo detector may be installed at a side opposite the position of the LED module, or may be installed at a side on the same plane as the position of the LED module. The photo detector may detect reflected or transmitted light derived from body parts depending on the relationship with the position of the LED module, and may measure the intensity of light. Accordingly, the signal collection unit 210 may observe a change in the intensity of light measured by the photo detector and measure the PPG signals based on the change in the intensity of light.

The feature extraction unit 230 may extract a plurality of features from the bio-signal. In other words, various pieces of feature information about bio-signals measured from the measurement subject being measured may be utilized as training data to construct a learning model utilized to estimate glycated hemoglobin non-invasively. The feature extraction unit 230 may acquire various pieces of feature information by analyzing bio-signals. For example, the feature extraction unit 230 may extract various features by applying frequency analysis, statistical analysis, and waveform analysis based on the bio-signals. In this connection, the feature extraction unit 230 may perform preprocessing operations such as sampling, filtering, and normalization on the bio-signals as needed.

In an embodiment, the feature extraction unit 230 may collect external features directly measured from the measurement subject being measured along with internal features directly extracted from the PPG signals and determine the same as a plurality of features. The feature extraction unit 230 may define a plurality of important and distinguishing features to increase the accuracy of non-invasive glycated hemoglobin estimation and extract the features based on the PPG signals of the measurement subject being measured. In particular, these features may include PPG signal-based physiological features, signal-directed features, and physical parameters.

In an embodiment, the feature extraction unit 230 may: extract, based on the PPG signals, Zero-Crossing Rate (ZCR), Auto Correlation, Power Spectral Density (PSD), Kaiser-Teager energy (KTE), Spectral Analysis (SA), Wavelet Analysis (WA), Autoregressive Coefficients (ARC), Heart Rate (HR), and Breathing Rate (BR) as the internal features; and collect Body Mass Index (BMI), Finger Width (FW), and Saturation Pulse Oxygen (SpO2) as the external features.

More specifically, the ZCR may correspond to a total number of sign changes (from positive to negative or vice versa) in a specific frame of the corresponding signal or the entire signal of the PPG, and may be expressed in Equation 1 below.

$$ZCR = \frac{1}{T-1}\sum_{c=1}^{T-1} 1_{\mathbb{R}<0}(s_t s_{t-1}) \quad \text{[Equation 1]}$$

In the equation above, $1_{R<0}$ represents the indicator function, and T represents the time length of the signal.

The Auto Correlation may correspond to the auto correlation of a time series variable (included in the data) over time. In other words, the periodic component of the signal may be acquired through auto correlation. In general, the Auto Correlation may correspond to a time-delayed version of the corresponding signal. For example, a time delay of 0 results in maximum auto correlation. The time domain version and frequency domain version of auto correlation may be expressed as Equations 2 and 3, respectively, below.

$$R_{ss}(\tau) = \int_{-\infty}^{\infty} s(t)s(t+\tau)dt \quad \text{[Equation 2]}$$

$$R_{ss}(\omega) = |S(\omega)|^2 \quad \text{[Equation 3]}$$

In the equation above, τ represents the time delay, and s(t) and S(ω) represent the PPG signal and the corresponding Fourier transform, respectively.

The PSD may correspond to the energy distribution over the various frequency components of a signal. Among various methods for calculating the PSD, a Welch method may be utilized. The PPG signals may be processed into frames by the Welch method. The Fourier transform of this sequence in each frame (k=1, 2, 3, . . . , K) may be expressed as Equation 4 below. In addition, in this way, the modified periodic rate may be expressed as Equation 5 below.

$$A_k(n) = \frac{1}{L}\sum_{m=0}^{L-1} s_k(m)W(m)e^{-\frac{2\pi jmn}{L}} \quad \text{[Equation 4]}$$

$$I_k(f_n) = \frac{L}{U}|A_k(n)|^2 \quad \text{[Equation 5]}$$

In this connection, the PSD may be calculated through Equation 6 below. Herein, the periodogram may be averaged, and the kurtosis, variance and mean of the PSD may be expressed as shape vectors.

$$\hat{P}(f_n) = \frac{1}{K}\sum_{k=1}^{K} I_k(f_n) \quad \text{[Equation 6]}$$

The KTE may be used to analyze the energy profile of the acquired PPG signal ㄴ while considering the signal frame as a periodic waveform. The KTE may be measured according to Equation 7 below. In addition, some statistical properties such as kurtosis, skewness, variance and mean of the energy profile may be calculated.

$$\Phi[s(n)] = s^2(n) - s(n+1)s(n-1) \quad \text{[Equation 7]}$$

The SA may analyze various frequency domain properties of the signal by taking the Fast Fourier Transform (FFT) of the input PPG signals. Herein, the flatness (kurtosis) and skewness of the frequency distribution may be considered as input features of the spectrum analysis.

In the WA, in order to obtain the features based on Continuous Wavelet Transform (CWT), the PPG signals may be modeled as a 'Mexican Hat Wavelet' as shown in Equation 8 below, and in the CWT, the absolute average may be calculated.

$$\varphi(t) = \frac{2}{\sqrt{3\sigma}\pi^{1/4}}\left(1 - \left(\frac{t}{\sigma}\right)\right)e^{\frac{t^2}{2\sigma^2}} \quad \text{[Equation 8]}$$

The ARC may be modeled through an autoregressive (AR) model. For example, the propagation of the PPG signals through vessels of different diameters (capillaries, veins, arteries) and viscosity may be modeled through an autoregressive model. In other words, a vector of length 5 (5th order AR model) may be extracted using the Yule-Walker equation. The general expression of the AR model may be expressed as Equation 9 below.

$$X_t = c + \sum_{i=1}^{p} \phi_i X_{t-i} + \epsilon_t \quad \text{[Equation 9]}$$

The HR may be measured by accurately sensing the peak position of the PPG signals. In other words, the HR may be calculated by calculating the continuous peak distance and using Equation 10 below.

$$HR = \frac{60}{t_{pp}} \quad \text{[Equation 10]}$$

The BR may be acquired by extracting three breathing-influenced parameters (in other words, amplitude, intensity, and frequency) from the PPG signals using an incremental merge segmentation algorithm, and then fusing these features by a smart fusion algorithm.

The BMI is closely related to diabetes, and thus may be included in the feature vector, which is training data for a machine learning model for estimating glycated hemoglobin or blood glucose. The BMI may correspond to an important physical parameter for a machine learning model for estimating glycated hemoglobin or blood glucose according to an embodiment of the present disclosure. The mathematical equation for calculating the BMI may be expressed as Equation 11 below.

$$BMI = \frac{\text{mass}}{\text{height}^2} \quad \text{[Equation 11]}$$

The FW may be an effective feature for both reflective and transmissive types. In the case of reflection, it is possible to predict the distance until the light irradiated to the finger returns, and in the case of transmission, it may also correspond to an important factor in predicting the distance that the light irradiated to the finger passes through the finger to the other end.

The Saturation Pulse Oxygen (SpO2) may correspond to the ratio of oxyhemoglobin in the blood. Calibration may generally be performed on the ratio R acquired through Equation 12 below. In the case of an embodiment of the present disclosure, the SpO2 value may be directly measured and utilized from the measurement subject being measured through a medical device (Schiller Argus OXM Plus).

$$R = \frac{(\text{AC}/\text{DC})_{\lambda_1}}{(\text{AC}/\text{DC})_{\lambda_2}} \quad \text{[Equation 12]}$$

The feature extraction unit 230 may derive the final feature vector as shown in Equation 13 below based on the features described above. In other words, a feature vector may be defined for each frame f of the PPG signals. In this connection, heart rate and respiratory rate may be used for decision-making to limit each signal to a good PPG signal.

$$X_F^f = \begin{bmatrix} s_{zcr}, s_{ACR}, s_{PSD}^{kurt}, s_{PSD}^{var}, s_{PSD}^{mean}, \\ s_{KTE}^{kurt}, s_{KTE}^{var}, s_{KTE}^{mean}, s_{KTE}^{skew}, \\ s_{spec}^{kurt}, s_{spec}^{skew}, s_{wavelet}^{mean}, s_{AR}, s_{spo2}, \\ s_{skew}, s_{sad}, BMI, FW \end{bmatrix} \quad \text{[Equation 13]}$$

In an embodiment, the feature extraction unit 230 may determine at least one representative feature according to importance among the internal features and determine a plurality of features by adding the external features to the representative features. In other words, the representative features may include Sum of Absolute Difference (SAD), Power Spectral Density Variance (PSD Variance), Kaiser-Teager Energy Variance (KTE Variance), and Zero Crossing Ratio (ZCR) among the internal features, and may include at least one of Body Mass Index (BMI), Finger Width (FW), or Saturation Pulse Oxygen (SpO2), which are external features. The feature extraction unit 230 may selectively determine 7 features with the highest importance from the existing 18 features. A machine learning model for estimating glycated hemoglobin may be constructed as a result of learning a feature vector defined only by representative features determined by the feature extraction unit 230. The number and type of representative features are not necessarily limited thereto, and may be applied variably as needed.

The model construction unit 250 may learn training data including a plurality of features to construct a machine learning model for estimating glycated hemoglobin or blood glucose. In other words, the model construction unit 250 may construct a machine learning model by learning the feature vector generated by the feature extracting unit 230 as training data. The process of constructing a machine learning model by the model construction unit 250 may be performed repeatedly until a preset learning amount is reached or the accuracy of the constructed model meets a predetermined standard.

In an embodiment, the model construction unit 250 may construct a machine learning model by learning training data composed of representative features. The training data used for learning may be implemented as a feature vector of a plurality of features, and the model construction unit 250 may selectively learn the seven features with the highest importance in estimating glycated hemoglobin or blood glucose as representative features to construct a machine learning model. In this connection, by selectively learning only a few features among a plurality of features, the learning process may be performed efficiently and high prediction performance may be achieved.

In cases where the measurement site of bio-signals corresponds to the wrist rather than the finger, features related to finger thickness may be selectively excluded from the learning process. In addition, the reference blood glucose value may correspond to the blood glucose level measured from the measurement subject being measured, and may be largely divided into fasting blood glucose and postprandial blood glucose. The reference blood glucose value may be used in the learning process of the machine learning model as needed.

The glycated hemoglobin/blood glucose estimation unit 270 may generate input data based on bio-signals extracted from the measurement subject being measured and input the input data to a machine learning model to estimate the glycated hemoglobin or blood glucose of the measurement subject being measured. When the construction of the machine learning model is completed, the glycated hemoglobin/blood glucose estimation unit 270 may utilize the same to perform a glycated hemoglobin or blood glucose estimation operation. The glycated hemoglobin/blood glucose estimation unit 270 may generate input data based on bio-signals extracted from the measurement subject to be measure and then input the input data to a machine learning model to generate an estimate of glycated hemoglobin or blood glucose as a result. In this connection, the input data may be generated based on the PPG signals collected over a predetermined period of time, and the time period or range of the PPG signals used to generate the input data may be variably applied as needed.

In an embodiment, the machine learning model may include a machine learning model trained using the Random Forest or XGBoost algorithm. This will be described in more detail with reference to FIGS. 5 to 7.

In an embodiment, the glycated hemoglobin/blood glucose estimation unit 270 may analyze the glycated hemoglobin or blood glucose to determine the diabetes grade of the measurement subject being measured. In other words, when glycated hemoglobin/blood glucose is estimated, the glycated hemoglobin/blood glucose estimation unit 270 may analyze the estimated glycated hemoglobin or blood glucose and may diagnose the measurement subject being measured into three grades (for example, normal, pre-diabetic, diabetic). For example, an estimated glycated hemoglobin of 6.5 or higher may be determined as a diabetes grade, 5.7 to 6.4 may be determined as a pre-diabetes grade, and 5.6 or less may be determined as a normal grade. As another example, based on fasting blood glucose, an estimate of blood glucose of 126 (mg/dl) or higher is determined as a diabetes grade, 110 to 125 (mg/dl) is determined as a pre-diabetic grade, and 70 to 110 (mg/dl) is determined as a pre-diabetic grade.

The control unit 290 may control the overall operation of the apparatus 130 for estimation of glycated hemoglobin or blood glucose and manage the control flow or data flow among the signal collection unit 210, the feature extraction unit 230, the model construction unit 250, and the glycated hemoglobin/blood glucose estimation unit 270.

Figure 3:
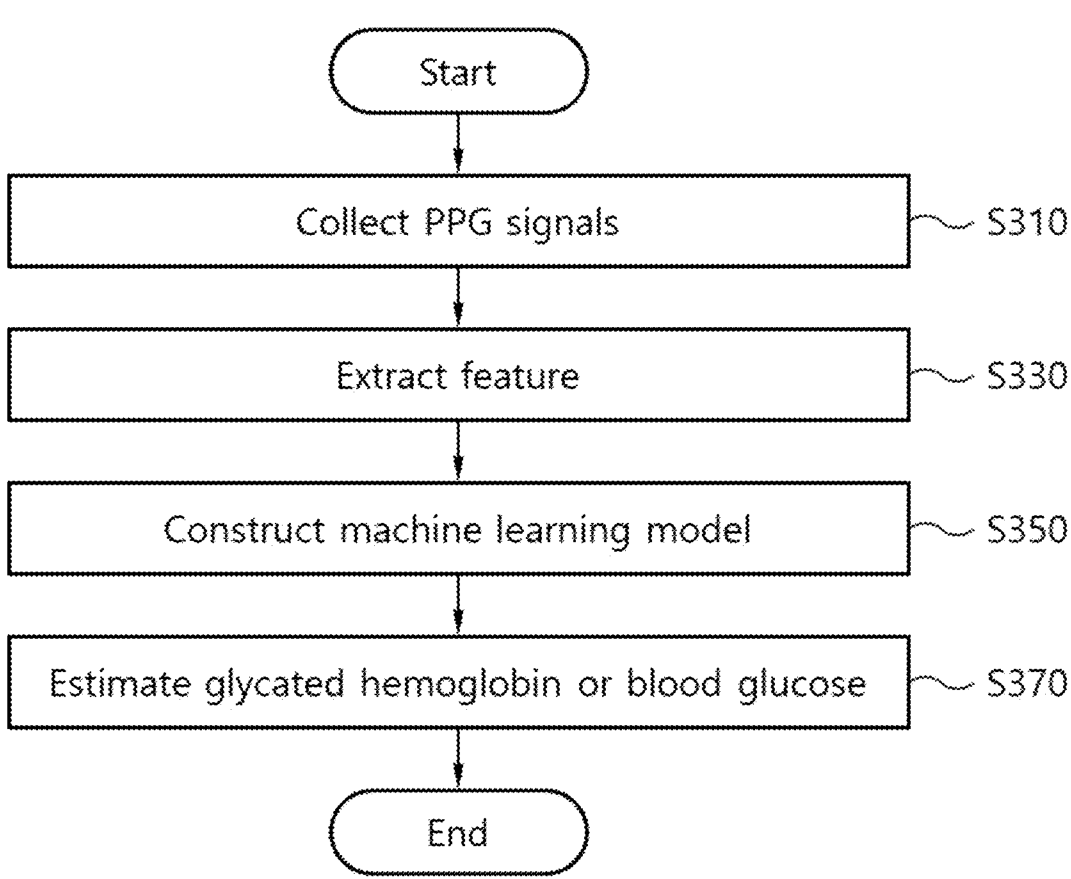
FIG. 3 is a flowchart explaining a process for non-invasive estimation of glycated hemoglobin or blood glucose according to an embodiment of the present disclosure.

FIG. 3 is a flowchart explaining a process for non-invasive estimation of glycated hemoglobin or blood glucose according to an embodiment of the present disclosure.

Referring to FIG. 3, the apparatus 130 for estimation of glycated hemoglobin or blood glucose may collect a bio-signal of the measurement subject being measured through the signal collection unit 210 (stage S310). The apparatus 130 for estimation of glycated hemoglobin or blood glucose may extract a plurality of features from the bio-signal through the feature extraction unit 230 (stage S330). The apparatus 130 for estimation of glycated hemoglobin or blood glucose may learn training data including a plurality of features through the model construction unit 250 to construct a machine learning model for estimating glycated hemoglobin or blood glucose (stage S350). The apparatus 130 for estimation of glycated hemoglobin or blood glucose may generate input data based on the bio-signal extracted from the measurement subject being measured through the glycated hemoglobin/blood glucose estimation unit 270 and input the input data to a machine learning model to estimate the glycated hemoglobin or blood glucose of the measurement subject being measured (stage S370).

Figure 4:
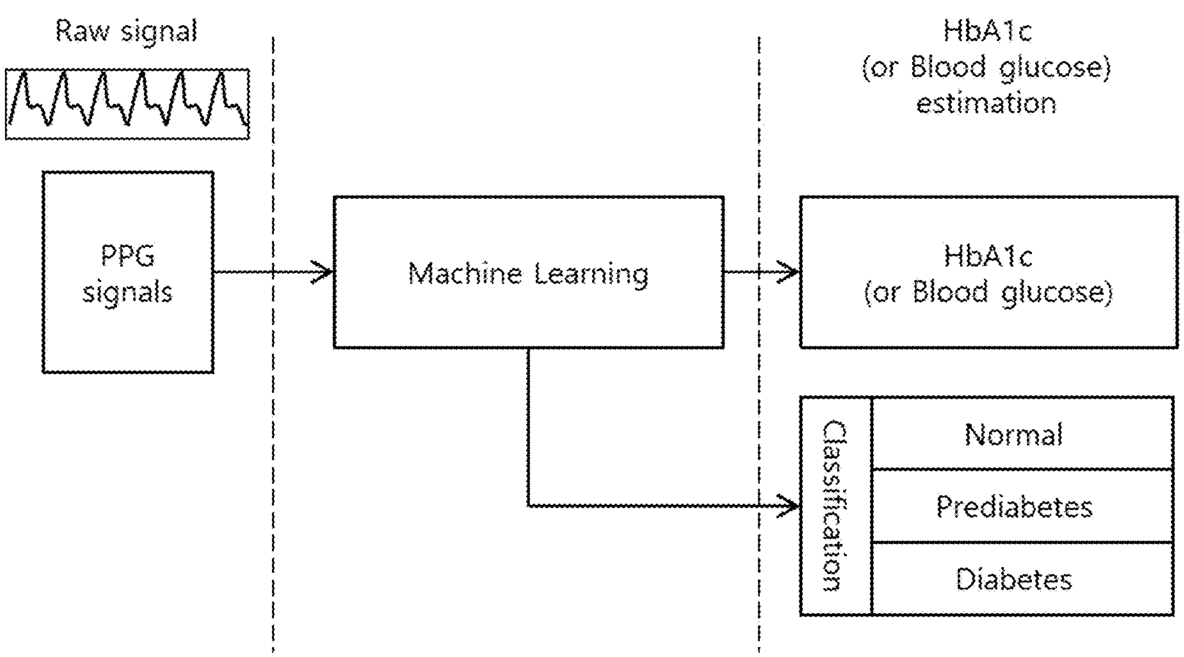
FIG. 4 is a diagram illustrating the entire learning system according to an embodiment of the present disclosure.

FIG. 4 is a diagram illustrating the entire learning system according to an embodiment of the present disclosure.

Referring to FIG. 4, the apparatus 130 for estimation of glycated hemoglobin or blood glucose may non-invasively estimate glycated hemoglobin or blood glucose utilizing a machine learning model. In this connection, the machine learning model used may be constructed by learning a feature vector generated based on the bio-signal of the measurement subject being measured, that is, PPG signals. The apparatus 130 for estimation of glycated hemoglobin or blood glucose may accurately estimate the concentration of glycated hemoglobin or blood glucose of the measurement subject being measured through a machine learning model, and may classify diabetes grade based on the estimated glycated hemoglobin or blood glucose value. In this connection, diabetes grades may be divided into three categories and defined. For example, the diabetes grade may be divided into normal, pre-diabetes, and diabetes, and the apparatus 130 for estimation of glycated hemoglobin or blood glucose may provide the diabetes grade of the measurement subject being measured with an estimation result based on the estimated glycated hemoglobin or blood glucose value.

Figure 5:
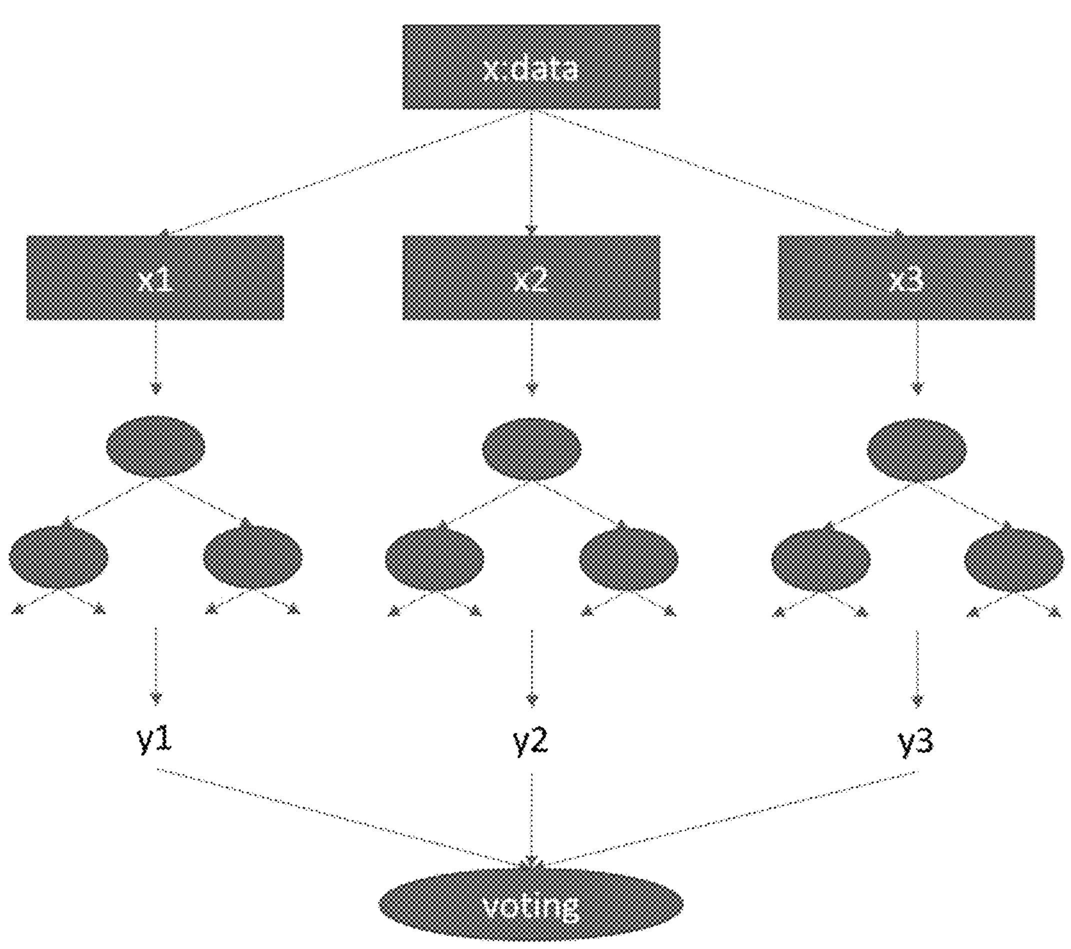
FIGS. 5 to 7 are diagrams illustrating the learning algorithm according to an embodiment of the present disclosure.
Figure 6:
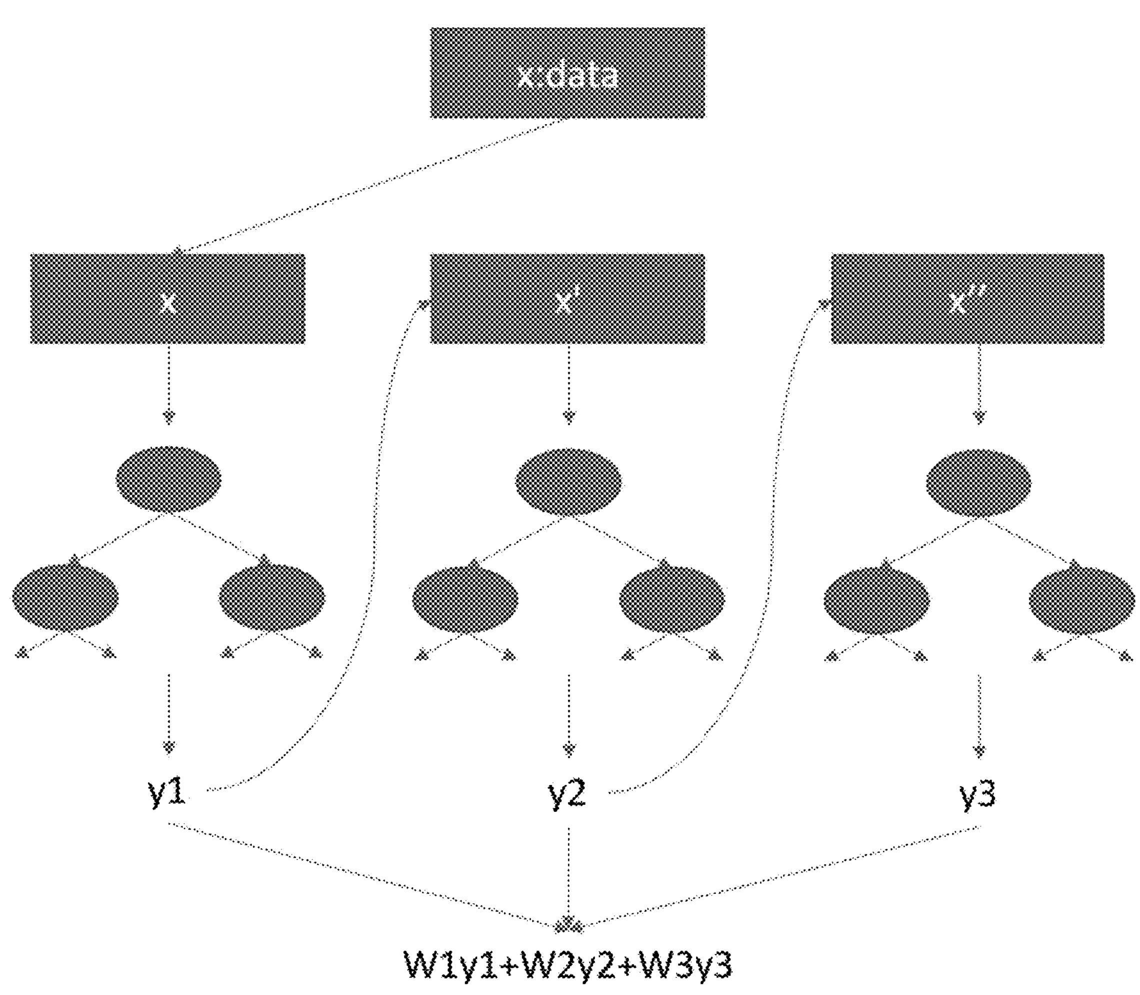
Figure 7:
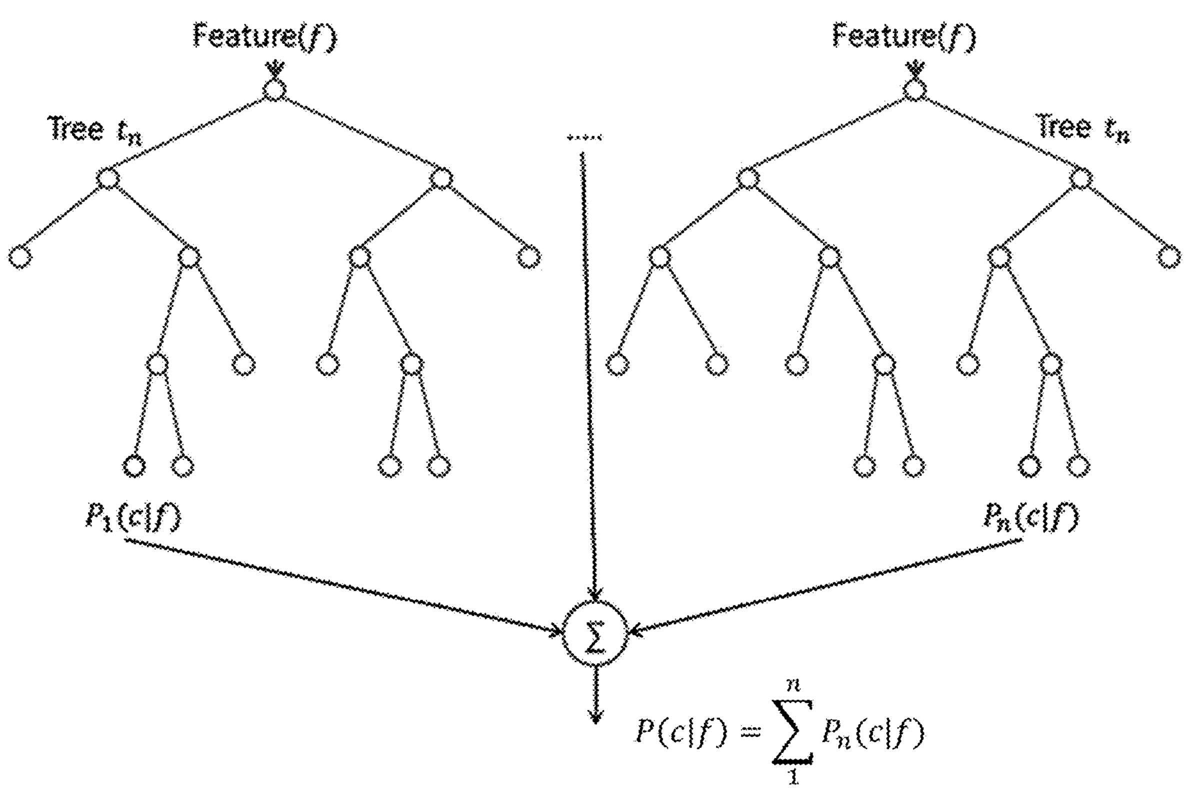

FIGS. 5 to 7 are diagrams illustrating the learning algorithm according to an embodiment of the present disclosure. FIG. 5 relates to bagging, FIG. 6 relates to boosting, and FIG. 7 relates to random forest.

Referring to FIG. 5, a method for estimation of glycated hemoglobin according to an embodiment of the present disclosure may construct a machine learning model utilizing two different regression algorithms. One may be Random Forest (RF) regression analysis, and the other may correspond to XGBoost (XGB). Both algorithms may correspond to ensemble machine learning models.

First, decision trees and ensembles will be explained. A decision tree may be a type of decision support tool that diagrams decision rules and their results in a tree structure. The decision tree may be used primarily in decision analysis to find the strategy that will produce the closest result to a goal. An ensemble may correspond to a method of combining multiple models and extracting the results. Rather than using a single strong model with high accuracy, the method is based on combining several weak models with low accuracy to achieve high accuracy. In addition, the ensembles may be classified into bagging and boosting depending on the method.

As shown in FIG. 5, when using multiple models, bagging may be implemented by calculating the values from each model to produce the final result values. In other words, input data x1, x2, and x3 based on data x may be input to independent models m1, m2, and m3, respectively, and the outputs of each model, y1, y2, and y3, may be acquired. In this connection, bagging may select the best result through voting for each output and determine the same as the final output.

Referring to FIG. 6, in boosting, data sampled from input data x may be input to model m1, where data (x) is first input. Among the results of y1, which is the output of model m1, the input data x may be updated by reflecting the weights for incorrectly predicted values, and the data sampled from updated x' may be input to the next model, m2. Likewise, the input data x' may be updated by reflecting the weights for incorrectly predicted values in the result of y2, which is the output of model m2, and the data sampled from the updated x" may be input to model, m3. Because the performance of each model is different, the final result may be generated by reflecting the weight W in each model. In FIG. 6, the final result according to boosting may correspond to W1*y*1+W2*y*2+W3*y*3.

Referring to FIG. 7, random forest may use the concept of bagging. In other words, multiple decision trees may be formed, new data points may be passed through each tree simultaneously, voting may be conducted on the results classified by each tree, and the result with the most votes may be selected as the final classification result. Some trees generated by random forests may be overfitting, but the impact of overfitting on prediction results may be reduced by generating a large number of trees. XGB may correspond to a gradient boosting algorithm. In other words, XGB may provide a parallel tree boosting function.

FIGS. 8A and 8B are diagrams illustrating performance comparison regarding glycated hemoglobin estimation according to an embodiment of the present disclosure.

Referring to FIG. 8A, the comparison results of diabetes determination performance may be checked for the case of using all 18 features and the case of using selected 7 representative features in non-invasive glycated hemoglobin estimation using machine learning according to an embodiment of the present disclosure. The top table of FIG. 8A may correspond to the results of finally extracting 7 representative features (Sum of Absolute Difference, PSD Variance, KTE Variance, Zero Crossing Rate, BMI, FW, SpO2) among the 18 features and applying the same to the glycated hemoglobin estimation process. Upon reviewing the prediction results for 18 features and the prediction results for 7 features, it was identified that the $R^2$ score of the XGBoost model for 7 features was the highest compared to other models. In addition, in the case of the bottom table of FIG. 8A, it was identified that the XGBoost model had the highest diagnostic performance for 7 features in diabetes diagnosis.

Referring to FIG. 8*b*, in the case of non-invasive glycated hemoglobin estimation using machine learning according to an embodiment of the present disclosure, when the measurement position corresponds to a body part other than the finger (for example, wrist, etc.), the features related to finger thickness may naturally be excluded from the learning and inference process. In FIG. 8B, it is possible to check the comparison results of diabetes determination performance when using all 17 features and when using only 6 representative features. FIG. 8B may correspond to the results of finally extracting 6 representative features (Sum of Absolute Difference, PSD Variance, KTE Variance, Zero Crossing Rate, BMI, SpO2) among the 17 features and applying the same to the glycated hemoglobin estimation process. Upon reviewing the prediction results for 17 features and the prediction results for 6 features, it was identified that the $R^2$ score of the XGBoost model for 6 features was the highest compared to other models.

Figure 9:
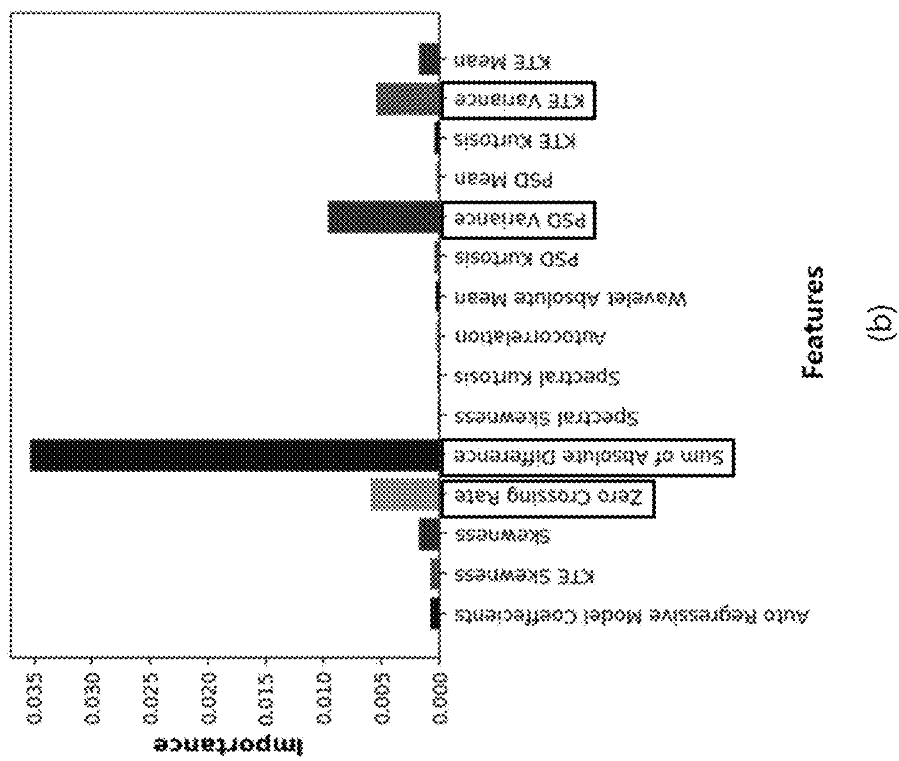
FIG. 9 is a diagram illustrating a feature importance graph related to glycated hemoglobin estimation according to an embodiment of the present disclosure.
Figure 9:
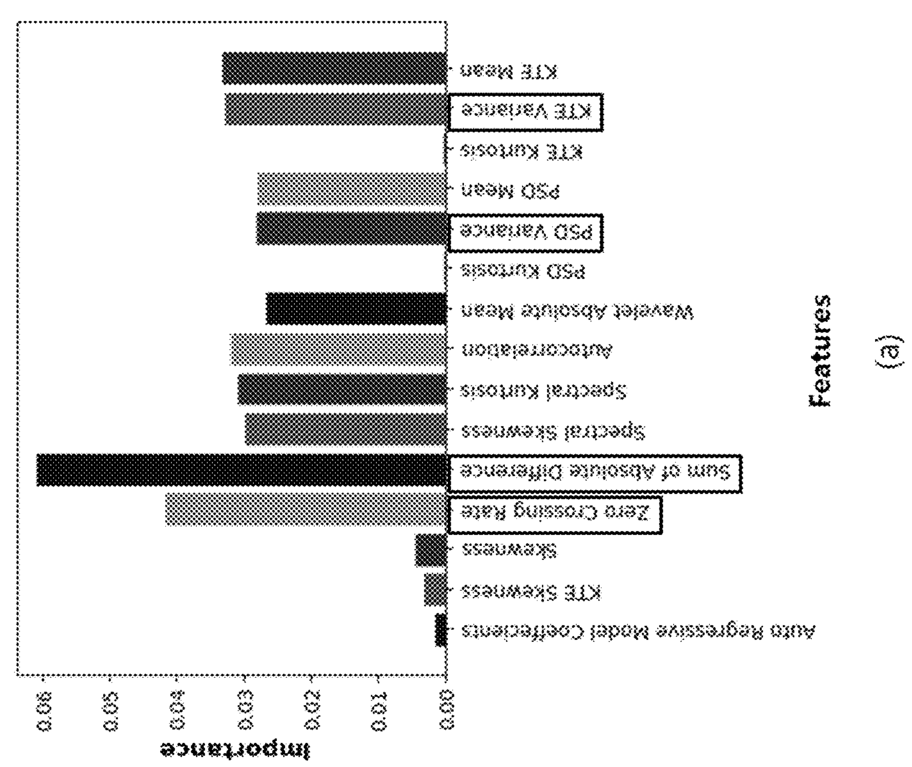

FIG. 9 is a diagram illustrating a feature importance graph related to glycated hemoglobin estimation according to an embodiment of the present disclosure.

Referring to (a) and (b) of FIG. 9, in estimating glycated hemoglobin, it is possible to identify an importance graph for features excluding BMI, FW, and SpO2, which are external input features, out of a total of 18 features. In the case of random forest, it was identified that the feature SAD had the highest importance, and the importance of representative features (highlighted by squares) appears similar to other features. In the case of XGBoost, it was identified that the importance of representative features, including SAD, was relatively high compared to other features. As a result, a machine learning model learned through XGBoost may achieve prediction performance similar to that of learning all features only by learning representative features.

FIG. 10 is a diagram explaining performance comparison regarding blood glucose estimation according to an embodiment of the present disclosure.

Referring to FIG. 10, in the case of blood glucose, the basic structure may be the same as the estimated glycated hemoglobin. In other words, a machine learning model may be constructed by learning a total of 18 features, including finger thickness (FW), and an additional machine learning model may be constructed by selecting 7 representative features. In addition, a machine learning model may be constructed using a total of 17 features excluding finger thickness (FW), and an additional machine learning model may be constructed by selecting 6 representative features (excluding FW). The top table in FIG. 10 may correspond to a performance comparison when all 17 features are used and when 6 selected representative features are used, and the bottom table in FIG. 10 may correspond to a comparison of diabetes determination performance when all 17 features are used and when 6 selected representative features are used.

FIG. 11 is a diagram illustrating a feature importance graph related to blood glucose estimation according to an embodiment of the present disclosure.

Referring to (a) and (b) of FIG. 11, in the case of blood glucose, it is possible to check an importance graph for features excluding BMI and SpO2, which are external input features, among 17 features. Herein, selection of representative features may be performed in the same way as for glycated hemoglobin. In addition, in the case of blood glucose, a total of 18 features and 7 representative features including finger thickness may be used, and a total of 17 features and 6 representative features may be used excluding finger thickness. As a result, the estimation process of glycated hemoglobin and blood glucose may be performed almost identically based on the same formula and stages.

Hereinbefore, although preferred embodiments of the present disclosure have been illustrated and described, it will be appreciated by those skilled in the pertinent technical field that various modifications and variations may be made without departing from the scope and spirit of the present disclosure as described in the claims below.

DESCRIPTION OF REFERENCE NUMERALS

100: System for estimation of glycated hemoglobin or blood glucose
110: User terminal 130: Apparatus for estimation of glycated hemoglobin or blood glucose
150: Database
210: Signal collection unit 230: Feature extraction unit
250: Model construction unit 270: Glycated hemoglobin/blood glucose estimation unit
290: Control unit

What is claimed is:

1. A method for non-invasive estimation of glycated hemoglobin (HbA1c) or blood glucose by using machine learning, the method comprising:

collecting a bio-signal by irradiating a body part of a measurement subject with light using an LED module, detecting transmitted or reflected light using a photodetector, and measuring photoplethysmography (PPG) signals based on a change in intensity of the detected light;

extracting a plurality of features from the PPG signals, including selecting at least one representative feature from internal features based on importance according to a predefined importance ranking or evaluation metric, and combining the representative feature with at least one external feature;

constructing a machine learning model by learning training data including the selected features, wherein the machine learning model comprises a model trained using a Random Forest or XGBoost algorithm; and generating input data based on the PPG signals of the measurement subject and inputting the input data to the machine learning model to estimate glycated hemoglobin or blood glucose.

2. The method of claim 1, further comprising collecting external features directly measured from the measurement subject being measured along with internal features extracted directly from the PPG signals and determining the same as the plurality of features.

3. The method of claim 2, further comprising:

extracting, based on the PPG signals, Zero-Crossing Rate (ZCR), Auto Correlation, Power Spectral Density (PSD), Kaiser-Teager energy (KTE), Spectral Analysis (SA), Wavelet Analysis (WA), Autoregressive Coefficients (ARC), Heart Rate (HR), and Breathing Rate (BR) as the internal features; and collecting Body Mass Index (BMI), Finger Width (FW), and Saturation Pulse Oxygen (SpO2) as the external features.

4. The method of claim 1, further comprising analyzing the glycated hemoglobin or blood glucose to determine a diabetes grade of the measurement subject being measured.

5. The method of claim 1, wherein the internal features include at least one of Zero-Crossing Rate (ZCR), Auto Correlation, Power Spectral Density (PSD), Kaiser-Teager energy (KTE), Spectral Analysis (SA), Wavelet Analysis (WA), Autoregressive Coefficients (ARC), Heart Rate (HR), or Breathing Rate (BR), and the external features include at least one of Body Mass Index (BMI), Finger Width (FW), or Saturation Pulse Oxygen (SpO2).

6. An apparatus for non-invasive estimation of glycated hemoglobin (HbA1c) or blood glucose by using machine learning, the apparatus comprising:

an LED module configured to irradiate light to a body part of a measurement subject;

a photodetector configured to detect transmitted light transmitted through the body part or reflected light reflected from the body part and to measure photoplethysmography (PPG) signals based on a change in intensity of the detected light;

at least one processor configured to:

extract a plurality of features from the PPG signals, including selecting at least one representative feature from internal features based on importance according to a predefined importance ranking or evaluation metric, and combining the representative feature with at least one external feature;

construct a machine learning model by learning training data including the selected features, wherein the machine learning model comprises a model trained using a Random Forest or XGBoost algorithm; and generate input data based on the PPG signals of the measurement subject and input the input data to the machine learning model to estimate glycated hemoglobin or blood glucose of the measurement subject; and a memory storing instructions that, when executed by the at least one processor, cause the at least one processor to perform the extracting, constructing, and generating.

7. The apparatus of claim 6, wherein the at least one processor is further configured to collect feature extraction unit collects external features directly measured from the measurement subject being measured along with internal features extracted directly from the PPG signals and determine the same as the plurality of features.

8. The apparatus of claim 7, wherein the at least one processor is further configured to:

extract, based on the PPG signals, Zero-Crossing Rate (ZCR), Auto Correlation, Power Spectral Density (PSD), Kaiser-Teager energy (KTE), Spectral Analysis (SA), Wavelet Analysis (WA), Autoregressive Coefficients (ARC), Heart Rate (HR), and Breathing Rate (BR) as the internal features; and collect Body Mass Index (BMI), Finger Width (FW), and Saturation Pulse Oxygen (SpO2) as the external features.

* * * * *